United States Patent
Watts et al.

(10) Patent No.: US 6,432,440 B1
(45) Date of Patent: Aug. 13, 2002

(54) PECTIN COMPOSITIONS AND METHODS OF USE FOR IMPROVED DELIVERY OF DRUGS TO MUCOSAL SURFACES

(75) Inventors: Peter James Watts; Lisbeth Illum, both of Nottingham (GB)

(73) Assignee: West Pharmaceutical Services Drug Delivery & Clinical Research Centre Limited, Nottingham (GB)

( * ) Notice: Subject to any disclaimer, the term of this patent is extended or adjusted under 35 U.S.C. 154(b) by 0 days.

(21) Appl. No.: 09/402,976

(22) PCT Filed: Apr. 20, 1998

(86) PCT No.: PCT/GB98/01147
§ 371 (c)(1),
(2), (4) Date: Jan. 20, 2000

(87) PCT Pub. No.: WO98/47535
PCT Pub. Date: Oct. 29, 1998

(30) Foreign Application Priority Data

Apr. 18, 1997 (GB) .............................. 9707934

(51) Int. Cl.[7] .............................. A61F 6/06; A61K 9/00; A61K 9/12; A61K 9/06
(52) U.S. Cl. .......................... 424/434; 424/46; 424/430; 424/45; 424/435; 424/436; 424/437; 424/427
(58) Field of Search ................................ 424/430, 434, 424/435, 436, 427, 44, 45, 46

(56) References Cited

U.S. PATENT DOCUMENTS

| | | | |
|---|---|---|---|
| 4,659,696 A | * | 4/1987 | Hirai et al. ................. 514/15 |
| 4,826,683 A | * | 5/1989 | Bates ......................... 424/641 |
| 4,915,948 A | | 4/1990 | Gallopo et al. |
| 4,983,385 A | | 1/1991 | Hasegawa et al. |
| 5,147,648 A | * | 9/1992 | Bannert ...................... 424/435 |
| 5,200,180 A | * | 4/1993 | Bannert ...................... 424/427 |
| 5,318,780 A | * | 6/1994 | Viegas et al. ............... 424/427 |
| 5,456,745 A | | 10/1995 | Roreger et al. |
| 5,457,093 A | | 10/1995 | Cini et al. |

FOREIGN PATENT DOCUMENTS

| | | |
|---|---|---|
| EP | 0 289 512 B1 | 11/1988 |
| EP | 0 306 454 A2 | 3/1989 |
| EP | 0 518 798 A2 | 12/1992 |
| JP | 62-236862 A | 10/1987 |
| JP | 62236862 A * | 10/1987 |

OTHER PUBLICATIONS

Rollin, et al., "Pectin" in Industrial Gums, Academic Press:New York pp. 257–293 (1993).*

Aspden, et al., "Chitosan as a nasal delivery system: the effect of chitosan solutions on in Vitro and in Vivo mucociliary transport rates in human turbinates and volunteers," J. Pharm. Sci. 86(4):509–13 (1997).

Axelos & Thibault, "The Chemistry of Low–Methoxyl Pectin Gelatin" in The Chemistry and Technology of Pectin, pp. 109–118, Academic Press: New York, 1991.

Aydin & Akbuga, "Preparation and evaluation of pectin beads," Int. J. Pharm. 137:133–36 (1996).

Brown, et al., "Spreading and retention of vaginal formulations in post–menopausal women as assessed by gamma scintigraphy," Pharm. Res. 14(8):1073–78 (1997).

Burgalassi, et al., "A novel mucoadhesive buccal drug delivery system," Proc. 1st World Meet. APGI/APV Budapest, 9/11 p. 839–40 (1995).

(List continued on next page.)

Primary Examiner—Thurman K. Page
Assistant Examiner—Rachel M. Bennett
(74) Attorney, Agent, or Firm—Akin, Gump, Strauss, Hauer & Feld, L.L.P.

(57) ABSTRACT

Liquid pharmaceutical compositions for administration to a mucosal surface, comprising a therapeutic agent and a pectin with a low degree of esterification are described. Such compositions gel, or can be adapted to gel, at the site of application in the absence of an extraneous source of divalent metal ions.

24 Claims, 2 Drawing Sheets

OTHER PUBLICATIONS

Chetoni, et al., "Veicoli oftalmici mucoadesivi: studio preliminare della farmacocinetica oculare 'in vivo'," *Boll. Chem. Farm.* 135:147–49 (1996).

Illum & Fisher, "Inhalation Delivery of Therapeutic Peptides and Proteins", (Adjei & Gupta, eds.) pp. 135–184, Marcel Dekker Inc.:New York (1997).

Illum, et al., "Bioadhesive Microspheres as a Potential Nasal Drug Delivery System," *Int. J. Pharm.* 39:189–99 (1987).

Illum, et al., "Chitosan as a novel nasal delivery system for peptide drugs," *Pharm. Res.* 11(8):1186–89 (1994).

Martindale, *The Extra Pharmacopoeia*, 31st Ed., The Pharmaceutical Press:London (1996).

Oechslein, et al., "Nasal delivery of octreotide: Absorption enhancement by particulate carrier systems," *Int. J. Pharm.* 139:25–32 (1996).

Popovici & Szasz, "Mucoadhesive gel with polyuranides for endonasal administration" in *Buccal and nasal administration as alternatives to parental administration, Minutes of a European Symposium* (Duchene, ed.), pp. 292–296 Sante:Paris, France (1992).

Potts, et al., "In vivo determination of the oesophageal retention of smart hydrogel," *Proceed. Intern. Symp. Control Rel. Bioact. Mater.* 24:335–36 (1997).

Rollin, et al., "Pectin" in *Industrial Gums* Academic Press:New York pp. 257–293 (1993).

Smart, et al., "An in–vitro investigation of mucosa–adhesive materials for use in controlled drug delivery," *J. Pharm. Pharmacol.* 36(5):295–99 (1984).

Walter, "Analytical and graphical methods for pectin" in *The Chemistry and Technology of Pectin* pp. 189–225, Academic Press: New York (1991).

* cited by examiner

PECTIN COMPOSITIONS AND METHODS OF USE FOR IMPROVED DELIVERY OF DRUGS TO MUCOSAL SURFACES

Priority is claimed under 35 U.S.C. §119 to PCT/GB98/01147, filed Apr. 20, 1998, which corresponds to GB 9707934.7 filed Apr. 18, 1997.

This invention relates to an improved system for the delivery of drugs to mucosal surfaces such as the nose, the eye, the vagina, the rectum and the back of the throat.

Administration of therapeutic agents to mucosa is well known in the art.

A variety of drugs may be administered to the nose, including those intended for the local treatment of nasal diseases, nasal vaccines, and those intended for systemic circulation. Because the nose has a reasonable surface area and a good blood supply, certain lipophilic drugs, such as nicotine and propranolol, can be absorbed rapidly into the blood, resulting in a bioavailability which is similar to that seen with intravenous injection. More polar drugs are less well absorbed, though absorption may be improved by the use of enhancing agents such as surfactants, powders such as microcrystalline cellulose, gelling microspheres (eg. starch), and the bioadhesive polymer, chitosan. Examples of these systems are well known in the art and have been reviewed by Ilium and Fisher in "*Inhalation Delivery of Therapeutic Peptides and Proteins*", Adjei and Gupta (eds.) Marcel Dekker Inc., New York (1997) 135–184.

In a similar fashion, it is useful to deliver therapeutic agents, such as drugs and vaccines, to the vaginal cavity for a systemic effect or for the local treatment of diseases (particularly infectious diseases such as candidiasis and bacterial vaginitis) as well as for prophylaxis of diseases (e.g. HIV). Locally acting formulations may also be used to deliver contraceptive and spermicidal agents.

Drugs may also be administered to mucosa in the eye and the rectum in order to achieve local effects or for systemic activity.

Considerable advantages in terms of improved efficacy are expected to be gained if a nasally administered formulation were capable of retaining a drug, a vaccine, or DNA intended for local effect, in the nose for relatively long time periods. Previous workers have used a variety of strategies for this purpose.

For example, Illum and others found that biodegradable microspheres based on materials such as starch could delay clearance to a period of hours as compared to a normal half life of clearance of about 10 to 15 minutes (Illum et al, Int. J. Pharm., 39 (1986) 189–199). Surprisingly, such systems were also found to give an improved absorption by affecting the integrity of the tight junctions of the epithelial cells in the nasal cavity and are expected therefore to be best suited to drugs acting systemically.

Similarly, Illum and others have shown that the bioadhesive material chitosan can modify mucociliary clearance with an increase in drug absorption (Illum et al, Pharm Res., 11 (1994) 1186–1189).

It would be most beneficial, due to ease of use and of administration, to have available a simple solution spray system that was suitable for the administration of drugs to the nose and, better still, for the drugs administered via such a system to have a long retention in the nasal cavity. The skilled person may envisage various strategies to this end, including the use of pharmacological agents that decrease mucociliary clearance by a direct effect on the action of cilia, such as cocaine, as well as formulation methods such as environmentally-responsive gels.

Liquids that gel in response to a change in environment are known to those skilled in the art. The environmental change can be temperature, pH or ionic strength or a combination of these factors. Examples of all of these systems can be found in the prior art literature (see, for example, the smart hydrogel from Gelmed as described by Potts et al in *Proceed. Intern. Symp. Control Rel.*, 24, 335 (1997)). However, the majority of these have been found to be unsuitable for nasal use in man because of factors such as irritation, discomfort (eg. administration of cold solutions), mucosal damage, an unwanted enhancement of drug absorption into the systemic circulation, and many are unavailable due to lack of regulatory approval.

In summary, it would present considerable advantages to provide a single component nasal delivery system, which was in the form of a liquid for ease of administration, and in particular one that gelled in the nose upon contact with the nasal tissues, which could be used to administer, and to modify absorption characteristics, of drugs (therapeutic agents) intended to act locally or systemically. It would also be desirable to provide a system which is well accepted by patients, does not enhance the absorption of drug intended for a local effect into the systemic circulation (as this could lead to side effects), and comprises materials that are approved by regulatory authorities.

Those skilled in the art will appreciate that there are similar problems to be solved in respect of drug delivery for the improved treatment of conditions that affect the vaginal cavity, the rectum, the eye, and the back of the throat, as well as for the improved delivery of vaccines to the local lymphoid tissue, or for the improved delivery of DNA for the transfection of epithelial cells.

For example, drugs intended for the treatment of vaginal infections, or drug free formulations intended to act as vaginal moisturising agents (especially useful in post-menopausal conditions), should spread well in the vaginal cavity and be retained for long periods of time. However, it has been reported that so-called bioadhesive formulations that are intended to be retained in the vaginal cavity for days can be expelled rapidly, with more that 80% of the dose leaving the vagina in less than 2 hours (Brown et al, 14, 1073 (1997)). Thus, it would be advantageous to provide a single component liquid composition that could be inserted into the vagina as a simple liquid and that gelled under the local environmental conditions to give good retention.

For rectal enemas, it would be most beneficial if the liquid enema formed a gel once applied, ensuring close contact with the local environment and preventing early discharge.

Similar problems may be identified in respect of administration to the eye, by virtue of the fact that liquid formulations are rapidly cleared from the eye through drainage down the naso-lacrymal duct. A single component liquid composition that gelled upon application to the eye would be advantageous for the treatment of conditions such as eye infections and inflammation.

Pectins are materials which are found in the primary cell wall of all green land plants. They are heterogeneous materials, with a polysaccharide backbone that is uniform as $\alpha$-1,4-linked polygalacturonic acid. Various neutral sugars have been identified in pectins such as xylose, galactose, rhamnose, arabinose.

A critical property of pectins, which is known to affect their gelation properties, is the extent to which the galacturonic acid units are esterified. The degree of esterification (DE) of pectins found naturally can vary considerably (from 60 to 90%). The term DE is well understood by those skilled in the art and may be represented as the percentage of the total number of carboxyl groups which are esterified, or as the methoxyl content of the pectin. The respective theoretical maximum for each is 100% and 16% respectively. DE as used herein refers to the total number of carboxyl groups which are esterified. Low DE pectins (ie. those having less than 50% esterification) are usually prepared by the de-esterification of extracted pectins, normally on a bench scale, by way of an enzymatic process, or, on an industrial scale, by the treatment with acid or ammonia in an alcoholic heterogeneous medium. For pectins with a low degree of methoxylation (DM; less than 45%) the gelation properties are known to depend on the DM and the molecular weight of the pectin. The chemistry of low methoxyl pectin gelation is described by Axelos and Thibault in "*The Chemistry and Technology of Pectin*", Academic Press, New York, pp. 109–118, (1991).

Various prior art documents discuss the potential use of pectin as a bioadhesive and gelling material. Studies by Smart et al, J. Pharm. Pharmacol. 36, 295 (1984) in relation to the adhesiveness of various materials to mucus have shown that pectin is poorly adhesive in in vitro tests. A tablet capable of adhering to the mucus membrane containing pectin has been described in EP 306 454. Oechslein et al (Int. J. Pharm., 139, 1994), 25–32), have described the potential of various powder formulations to enhance the nasal absorption of the somatostatin analogue peptide octreotide. Pectin (type FPA) powder was used, and gave rise to an increase in the absolute bioavailability of the drug as compared to the drug administered in a saline solution. In none of these documents was the use of a solution formulation containing a pectin with a low DE, or a pectin that gels in contact with nasal secretions, described.

Pectin has also been studied as a mucoadhesive ophthalmic material by Chetoni et al (Bull. Chem. Farm., 135, 147 (1996)). Salt complexes of drugs with pectin for administration to the oral mucosa as patches have been described by Burgalassi et al, World Meet. Pharm. Biopharm. Pharm. Technol., (1995), p. 839, APGI, Paris. Popovici and Szasz (in "*Buccal and Nasal Administration as Alternatives to Parenteral Administration*", Minutes of a European Symposium (1992), Duchene, D., Ed., Sante, Paris, France. p. 292–6) have described mucoadhesive hydrogels containing cellulose and pectin and a bivalent cation in the form of magnesium. The use of a low DE pectin as a solution that would gel in contact with mucosal surfaces was not described in any of these documents.

U.S. Pat. No. 4,826,683 describes a nasal decongestant containing vegetable oil, aloe vera, zinc, vitamin C, vitamin A, vitamin E, vitamin B6, biotin and fruit pectin. The content of fruit pectin was to a maximum of 2 g per litre. The solubilised fruit pectin supplied by General Foods under the trade name "Certo" was preferred. JP 62236862 describes an artificial mucus composed of a mixture of a spinnable water soluble polymer and a polysaccharide, protein or vinyl polymer. Pectin is listed as a suitable polysaccharide, though the type of pectin is not specified.

U.S. Pat. No. 5,147,648 (EP 289 512) describes a pharmaceutical formulation made from at least two components which, when added separately, can form a gel for treating a mucosa. The two components are applied separately to the same area of a mucous membrane. The components may be added simultaneously or sequentially. One of the gel forming solution components includes a calcium salt (eg. calcium gluconate) and the other may include a pectin. There is no suggestion in this prior art document that a solution comprising pectin may be administered as a single component, in the absence of a separately applied solution of calcium ions, which will gel once in contact with the mucosa.

U.S. Pat. No. 5,318,780 describes aqueous pharmaceutical vehicles containing two components, a film forming polymer (eg. pectin) and an ionic polysaccharide, which are then gelled in situ by contacting the mixture with a counter-ion. Polygalacturonic acids such as pectin are mentioned in an extensive listing of representative useful polymers for application in the eye as corneal mastis protective corneal shields. No examples of the use of a pectin solution alone, nor of pectins with a low DE, or pectins that would gel in contact with the mucosa, are disclosed.

The preparation of pectin beads by ionotropic gelation has been described by Aydin and Akburfa (1996) Int. J. Pharm., 137, 133–136.

In summary, although it is known in the art that all pectins will form gels in the presence of calcium ions, for the pectins employed previously in pharmaceutical systems to be applied to mucosal surfaces, it has been hitherto understood that high levels of calcium are needed, which levels are well above physiological concentrations. This has necessitated the utilisation of pectin systems which are applied either in the form of preformed gels, or before or after the addition of exogenous calcium in order to produce a gel in situ. That liquids (especially solutions) comprising low DE pectins may be applied as such, and may gel upon, or just after, application to mucosa is neither described nor suggested in any of the aforementioned prior art documents. Further, the importance of the DE of pectin upon such gelation properties is not mentioned in any of these prior art documents.

We have now found, surprisingly, that certain pectin materials, namely those with a low DE, may be administered in the form of single component, simple liquid formulations (i.e. in an aqueous carrier) which will gel, or can be readily adapted to gel, upon application to mucosa in the nasal, rectal and vaginal cavities, in the eye, or at the back of the throat. We have also found, surprisingly, that gelation may occur at physiologically acceptable pH values in the presence of very much reduced calcium concentrations, ie. those which can be found physiologically in the nasal secretions, as well as in the vaginal lumen, the rectal cavity and the tear fluid of the eye.

According to a first aspect of the invention there is provided a single component liquid pharmaceutical composition for administration to a mucosal surface comprising a therapeutic agent, a pectin with a low DE and an aqueous carrier, that gels or can be adapted to gel at the site of application.

We have found, in particular, that such compositions gel, or can be adapted to gel, at the site of, and upon, or just after, application to a mucosal surface in the absence of an extraneously (ie. separately and/or independently) applied (simultaneously or sequentially) solution of calcium (or other divalent metal) ions. There is thus provided a single component liquid pharmaceutical composition for application directly to a mucosal surface comprising a therapeutic agent, a pectin with a low DE and an aqueous carrier, which composition is adapted to gel at the site of application in the absence of an extraneous source (eg. solution) of divalent metal ions applied to the same site.

According to a further aspect of the invention, there is provided a kit of parts comprising a liquid pharmaceutical composition for administration to a mucosal surface, comprising a therapeutic agent, a pectin with a low DE and an aqueous carrier, provided that the kit does not comprise a solution of divalent metal ions to be added extraneously to said surface.

In particular, there is provided a kit of parts comprising a liquid pharmaceutical composition for administration to a mucosal surface, which composition comprises a therapeutic agent, a pectin with a low DE and an aqueous carrier, and which kit of parts is packaged and presented with instructions to administer said composition to said surface in the absence of an extraneous source of divalent metal ions.

The liquid pharmaceutical compositions for administration to mucosal surfaces comprising therapeutic agent, low DE pectin and aqueous carrier, which are, or are to be, administered as a single component, and which gel, or are adapted to gel, in the absence of an extraneous source of divalent metal ions are referred to hereinafter as "the compositions of the invention".

By "liquid" composition, we mean a composition which is in the form of a mobile fluid upon application to the mucosa. The compositions of the invention are in the form of an aqueous formulation comprising a solution, a suspension, or an emulsion, including pectin and therapeutic agent, in water. The compositions of the invention will gel, or may be adapted to gel, upon, or shortly (eg. up to 5 minutes) after, application, to a form a solid or semi-solid gel material, which gel is suitable to provide a retaining effect at the site of administration.

By "degree of esterification (DE)", we mean the percentage of galacturonic acid units which are esterified, for example as described in the article by Walter in "*The Chemistry and Technology of Pectin*", Academic Press, New York (1991), p. 192. By "low DE", we mean a pectin in which less than 50%, and more preferably less than 35 of the galacturonic acid units are esterified.

By "extraneous source" of divalent metal ions, we include a separate and/or independent (ie. exogenous) source of such ions. Ions which are present in a gel resulting from administration of a composition of the invention to a mucosa are not derived from either the composition, or from the bodily secretions of the patient to which the composition is to be applied (eg. endogenous ions derived from nasal secretions, tear fluid, etc.). Divalent metal ions which may be mentioned include calcium ions.

According to a further aspect of the invention, there is provided a pharmaceutical gel composition obtainable by applying a liquid composition, comprising a therapeutic agent, a pectin with a low DE and an aqueous carrier, to a mucosal surface of a mammalian patient in the absence of extraneous application of a solution of divalent metal ions to said surface.

The gels so formed upon contact with mucosal surfaces will contain only endogenous divalent metal ions (i.e. those derived directly from bodily secretions) and will not include exogenous divalent metal ions (i.e those derived from an extraneous source). According to a further aspect of the invention there is provided a pharmaceutical gel composition, which gel comprises a therapeutic agent and a pectin with a low DE, which gel is obtainable by applying a liquid composition, comprising said therapeutic agent and pectin in an aqueous carrier, to a mucosal surface, and which gel is substantially free of divalent metal ions derived from an extraneous source applied to said mucosal surface before, or at the same time as, or after, said liquid composition is applied.

Because the compositions of the invention are not added in conjunction with an extraneous source of such ions, by "substantially free" of divalent metal ions, we mean greater than 97%, preferably greater than 99%, more preferably greater than 99.9%, and especially greater than 99.99% free.

Pectins with a low DE can be obtained from known sources, or can be obtained via de-esterification of high DE pectins (which may be obtained from, for example, Sigma Fine Chemicals), in accordance with known techniques, such as those described in the article by Rollin in "*Industrial Gums*", Academic Press, New York (1993) p. 257, or as described hereinbefore. Low DE pectin may, for example, be obtained from Copenhagen Pectin A/S as the commercial material known as Slendid Type 100 and Slendid Type 110. These pectins have been extracted from citrus peel and standardised by the addition of sucrose. The standardisation process is as described by Rollin in the abovementioned article. The DE is less than 50% for both pectins and of the order of 10% for type 100 and 35% for type 110. Further materials which may be employed include GENU pectin types LM 1912 CS and Pomosin pectin types LM 12 CG and LM 18 CG.

The compositions of the invention may be prepared by dissolving or dispersing the pectin of low DE and therapeutic agent in an aqueous system, to form a solution, a suspension or an emulsion in accordance with known techniques. For example, the therapeutic agent may be dissolved in a prior prepared aqueous solution of the pectin, or may be added as, or to form, a suspension in an aqueous system, where the drug particles are less than 100 microns in size, preferably between 1 and 20 microns. Alternatively, drug may be dissolved or suspended in a suitable is oily vehicle such as a vegetable oil, and then dispersed into the aqueous pectin solution to form an emulsion. It will be appreciated by those skilled in the art that the type of aqueous formulation so developed will depend upon to mucosa to be treated, as well as the dose, and the physical characteristics and properties, of the drug (e.g. its solubility, basicity etc.).

The concentration of low DE pectin in compositions of the invention depends upon the nature of the pectin, the presence of other components, and other factors which influence gelation properties of the composition (see below), but may be from 1 g/L to 100 g/L, and is preferably from 1 g/L to 50 g/L, more preferably from 2 g/L to 10 g/L and especially from 5 g/L to 10 g/L.

Compositions of the invention may be used with a view to the prevention of a major problem in the delivery of drugs to the nose for local treatment, namely the rapid mucociliary clearance mechanism. This natural process, which removes deposited material from the front of the nose to the throat, can clear material from the nose with a half-time of about 10 to 20 minutes. Such clearance rates can be measured readily in man using the saccharin clearance test or by gamma scintigraphy (Aspden el al, J. Pharm. Sci., 86, 509 (1997); Illum et al, Int. J. Pharm., 39 (1987) 189–199).

Compositions of the invention may be employed to retain a therapeutic agent which is intended to act locally at a mucosal surface for a relatively long period when compared to mucosal delivery systems known in the art. If the therapeutic agent is easily absorbed, absorption may be retarded, thus keeping more of the drug at the site of application, where it is needed.

Therapeutic agents which may be employed in the compositions of the invention include, for nasal administration, drugs that are employed locally to treat conditions such as rhinitis, viral infections, as well as those which act as decongestants. The compositions of the invention may also be used as a way of improving the delivery of vaccines to the nose associated lymphoid tissue and for the better presentation of DNA for the transfection of nasal epithelial cells.

The following list of therapeutic agents are suitable for use in the compositions of the invention, for local treatment of a mucosal surface, is provided by way of illustration and is not meant to be exclusive: antiviral agents such as ICAM-1, pirovadir, acylovir, bromovinyldeoxyuridine, α, β and γ-interferon, zidovudine; decongestants such as oxymetazaline, antiallergic agents, such as sodium cromoglycate and budesonide; steroids, such as fluticazone; vaccines, such as DNA, influenza, pertussis, measles and diphtheria vaccines; antibacterial agents, antifungal agents, such as ampliotericin, nystatin; contraceptive and/or spennicidal agents; antibodies especially for the treatment of RSV infection in children; prophylactic agents against HIV; antihistamines, such as diphenhydramine hydrochloride; genes.

Combinations of the abovementioned therapeutic agents may also be employed.

Compositions of the invention may also be employed to control the plasma level versus time profile for readily absorbable drugs which are intended to act systemically (ie. to give a flatter profile), either by altering the rate of transport into the general circulation, or by retarding absorption of readily absorbable drugs. This can, for example, be of importance when side effects from high peak plasma levels are to be avoided.

The compositions of the invention may thus be used for the modification of the systemic absorption of mucosally administered drugs, including, but not limited to, apomorphine, nicotine, hyoscine hydrobromide, lignocaine, fentanyl, naratriptan, pheromones and propranolol.

Combinations of the abovementioned therapeutic agents may also be employed.

For the avoidance of doubt, the term "therapeutic agents" is intended herein to include agents which are suitable for use in the treatment, and in the prevention, of disease.

The compositions of the invention may be used to treat/prevent diseases/conditions in mammalian patients depending upon the therapeutic agent(s) which is/are employed. For the above, non-exhaustive lists of locally acting and systemic drugs, diseases/conditions which may be mentioned include those against which the therapeutic agent(s) in question are known to be effective, and include those specifically listed for the drugs in question in Martindale, "The Extra Pharniacopoeia", 31st Edition, Royal Pharmaceutical Society (1996).

Preferred drugs include nicotine and apomorphine.

The amount of therapeutic agent which may be employed in the compositions of the invention will depend upon the agent which is used, and the disease to be treated, but may be in the range 0.01 to 40% w/w. However, it will be clear to the skilled person that suitable doses of therapeutic agents can be readily determined non-inventively. For example, estimates of dosage can be made from known injectable products assuming that from 0.1 to 90% of the dose is absorbed. Suitable single unit doses are in the range 10 $\mu$g to 500 mg depending upon the therapeutic agent(s) which is/are employed and the route of administration. Suitable daily doses are in the range 10 $\mu$g to 1 g/day depending upon the therapeutic agent(s) which is/are employed and the route of administration.

Most compositions comprising drug and a low DE pectin will gel upon application at the site of application, i.e. upon, or shortly (e.g. up to 5 minutes) after, contact with the relevant mucosal surface. However, in some formulations, the nature of the drug and/or the pectin which is/are employed may require that the composition is adapted such that it gels upon, or shortly (e.g. up to 1 minute) after, contact. This may be achieved readily via techniques which are well known to those skilled in the art:

For example, the concentration of pectin may be selected such that the aqueous formulation will gel once in contact with the mucosal surface.

Furthermore, the addition of monovalent ions to aid the gelling process may be required (for example, simple monovalent electrolytes, eg. NaCl, may be added to adapt the liquid formulation to gel, as well as to provide isotonicity).

The quantity and nature of the drug in the aqueous formulation may also have an influence on the gelation properties. For example, the addition of a high level of a certain drugs, including those which are weak bases (such as nicotine), which are known to form reversible complexes with anionic materials such as pectin, may require a change in the ratio between drug and pectin, so that preferably 30%, more preferably 50%, and most preferably 60%, of the negative charges on the pectin molecule are uncomplexed.

Alternatively, sugars in the form of, for example, sucrose can be added to the formulation to aid gelation. Non-ionic polysaccharides (such as hydroxypropyl methyl cellulose) may also be used.

The pH of the composition has also been found to affect gelation properties. The pH of the compositions of the invention may be from 2 to 9, more preferably from 3 to 8 and most preferably from 4 to 7, taking into account the gelation properties of the composition and the properties of the therapeutic agent. For example, in general, we have found that the lower the DE of the pectin, the lower the pH at which the composition will gel. pH may be adjusted in accordance with techniques which will be well known to those skilled in the art, such as the addition of pharmaceutically acceptable buffering agents, especially those of low ionic strength. Axelos and Thibault in "The Chemistry and Technology of Pectin", Academic Press, New York, pp. 109–118, (1991) describe how the gelation properties of low DE pectin solutions are somewhat sensitive to pH and ionic strength.

The abovementioned techniques, which may be used to adapt the compositions of the invention to gel, may be investigated and determined in the normal course of routine experimentation by those skilled in the art. Combinations of these techniques may also be employed in order to affect gelation properties.

The compositions may also contain other additives in the form of pharmaceutical excipients, such as preservatives (e.g. low concentrations of materials such as sodium metabisulphate), stabilisers, flavouring agents, absorption enhancers such as bile salts, phospholipids, as well as agents which are known to interact with the drug, for example to form inclusion or salt-bridge complexes, and promote a controlled release in the nasal cavity from the formed gel, such as cyclodextrins and ion exchange resins. Additional pharmaceutically acceptable excipients which may be added to the compositions of the invention include agents such as glycerol.

According to a further aspect of the invention there is provided a process for the preparation of a composition of the invention which comprises mixing together the therapeutic agent and the pectin in the aqueous carrier.

The compositions of the invention may be administered in suitable dosage forms, in accordance with techniques, and via delivery devices, all of which are known to those skilled in the art. For example, for nasal delivery, the compositions of the invention are preferably administered by way of a spray device, for example the Pfeiffer metered dose pump or the Valois metered dose pump, or via a liquid free flow system (such as nasal drops). For vaginal and rectal administration (infusion) a syringe-type applicator may be used, or plastics ampoules fitted with a suitable nozzle, where the contents of the ampoule can be delivered to the vaginal or rectal surface via the application of a slight pressure. Suitable systems for delivery of the compositions of the invention to the back of the throat include spray devices which are well known to those skilled in the art. Suitable systems for delivery of the compositions of the invention to eye include liquid free flow system which are well known to those skilled in the art (such as eye drops).

The compositions of the invention have the advantage that they may be readily administered to mucosal surfaces in the form of single component, simple liquid formulations, in the absence of an additional component comprising an extraneous source of divalent metal ions, using devices which are well known to those skilled in the art. The compositions of the invention also have the advantage that they gel upon, or shortly after, contact with mucosa, at physiologically acceptable pHs, in the presence of endogenous calcium (only) found physiologically in the nasal secretions, as well as in the vaginal lumen, the rectal cavity and the tear fluid of the eye.

Compositions of the invention also have the advantage that they may be used to retain a locally-acting drug at a mucosal surface, or to control drug absorption into the systemic circulation.

Compositions of the invention may also have the advantage that they may be well accepted by patients, and may comprise materials that are approved by regulatory authorities.

According to a further aspect of the invention there is provided a method of treatment of a patient which comprises the administration of a liquid pharmaceutical composition, comprising a therapeutic agent, a pectin with a low DE and an aqueous carrier, which composition gels or is adapted to gel at the site of application, to a mucosal surface of said patient in the absence of extraneous application of a solution of divalent metal ions to said surface.

There is provided further a method of treatment or prophylaxis of a disease which comprises administration of a composition of the invention including a therapeutic agent which is effective against said disease to a mucosal surface of a patient in need of such treatment in the absence of extraneous application of a solution of divalent metal ions to said surface.

The invention is illustrated, but in no way limited, by the following examples with reference to the figures in which.

EXAMPLE 1

Figure 1:
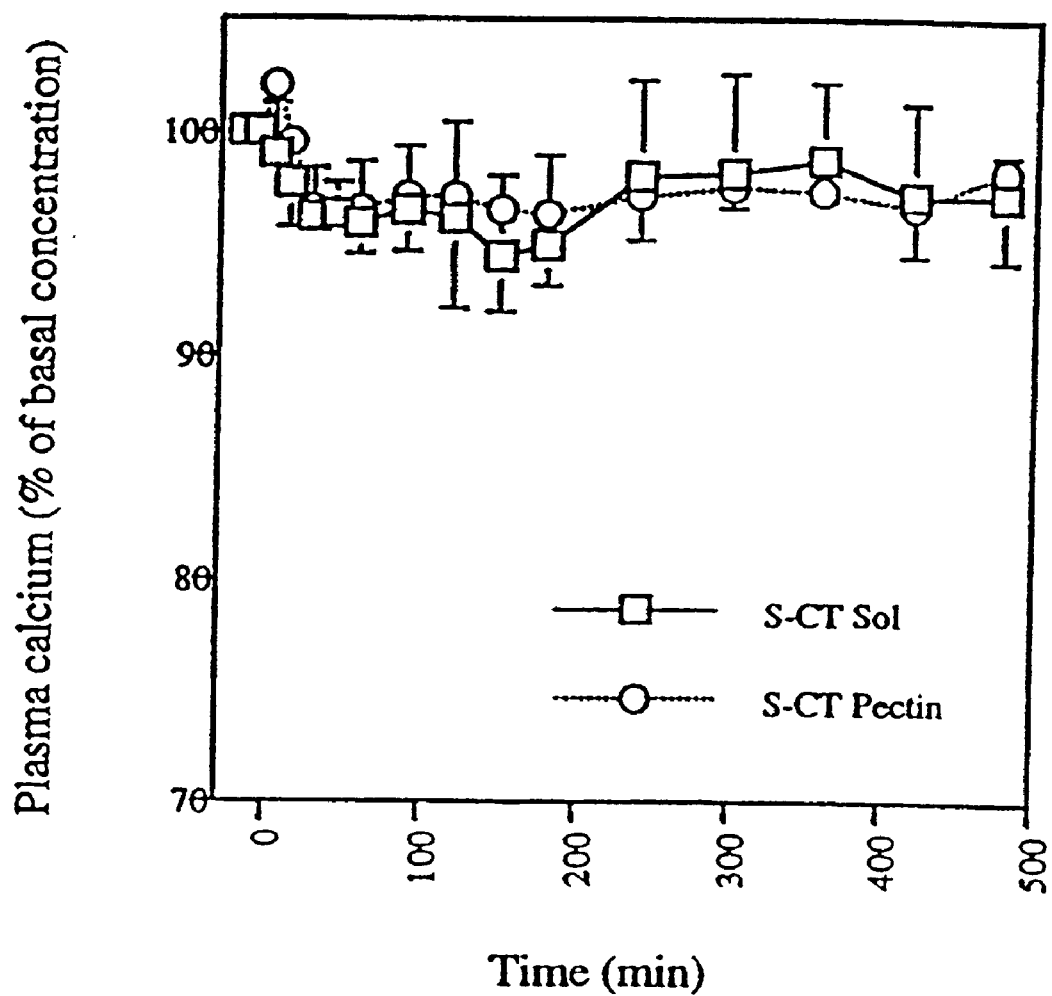
FIG. 1 shows the effect of systemic uptake of salmon calcitonin when administered intranasally to sheep in formulations comprising low DE pectin.

To Demonstrate that Pectins with Low DEs Gel Under Simulated Conditions of the Nasal Cavity while Pectins with Higher DEs Do Not Materials:
Pectin, esterified, potassium salt (DE: 31%; lot 22H0548; Sigma)
Pectin, esterified, potassium salt (DE: 67%; lot 74H1093; Sigma)
Pectin, esterified (DE: 93%; lot 125H0123; Sigma).
Pectin, Slendid type 100 (lot 620970; Hercules; Denmark).
Pectin, Slendid type 110 (lot 626790; Hercules, Denmark).
Pectin, GENU type LM 12 CG (lot G 63481; Pomosin GmbH; Hercules;, Germany).
Pectin, GENU type LM 18 CG (lot G 63484; Pomosin GmbH; Hercules; Germany).
Sodium chloride (BDH).
Potassium chloride (BDH).
Calcium chloride dehydrate (Sigma).

A simulated nasal electrolyte (SNES) solution was prepared, composed of the following ingredients:

| | |
|---|---|
| Sodium chloride | 8.77 g/L |
| Potassium chloride | 2.98 g/L |
| Calcium chloride dehydrate | 0.59 g/L |

The SNES was prepared in double strength:
3.508 g of sodium chloride, 1.192 g of potassium chloride and 0.236 g of calcium chloride dehydrate were weighed into three weighing boats respectively, and dissolved and transferred into a 200 mL volumetric flask.
The solution was stirred on a magnetic stirrer until the drug had dissolved.
Water was added to volume.

Preparation of 20 g/L Pectin Solutions
1 g of each type of pectin was weighed into a 100 mL bottle.
50 mL of ultrapure water was added to each bottle.
The content was stirred on a magnetic stirrer until pectin had dissolved, and
the pH of the solution was measured and adjusted to pH 4 or pH 6.5 with 0.1M sodium hydroxide solution.

Preparation of various formulations containing SNES and pectin with different concentrations (2 to 10 g/L)
Appropriate volumes of 20 g/L pectin solution, to obtain the final concentrations of 2, 3, 4, 5, 6, 7, 8, 9 and 10 g/L, were measured in a series of 10 mL screw capped glass tubes.
Appropriate volumes of water were added to obtain a total volume of 2.5 mL firstly, then 2.5 mL of the two fold concentration SNES was added.
The tubes were cooled in an ice water bath for 15 minutes.
The test tubes were tilted to check the phase state and flow property.
The tubes were vigorously shaken to check the phase state and flow property again.

Results
The results are shown in Table 1:
1. Pectin type 100 and 110 gelled with simulated nasal electrolyte solution when the final concentration of pectin was >2 g/L and formed a strong gel when the final concentration was >4 g/L at pH values of 4 and 6.5. The gel was transparent and homogeneous. The strength of gel increased with the increasing pectin concentration in system.
2. Pectin type LM 12 CG and LM 18 CG gelled at final pectin concentrations of 4 g/L and 6 g/L (pH 4) and 4 g/L (pH 6.5) respectively. These two pectin types only formed solid gels at pH 6.5 and at concentrations higher than 6 g/L and 8 g/L respectively.
3. Pectin with a DE of 31% (Sigma) gelled at a concentration of >2 g/L and formed a solid gel at concentrations >4 g/L. Pectin 67% and 93% did not form solid gels at concentrations up to 10 g/L at neither pH 4 nor at pH 6.5.

TABLE 1

Summary of simulated nasal electrolyte solution (SNES) - pectin system

| Supplier | Pectin type | Esterification degree (%) | pH of 20 g/l pectin | The lowest pectin concentration for gelling (g/l) | The lowest pectin concentration for forming a solid gel (g/l) |
| --- | --- | --- | --- | --- | --- |
| Hercules (Denmark) | SLENDID type 100 | 15 | 4.25 (original pH) | 2 | 4 |
| | | | 6.50 (adjusted pH) | 2 | 4 |
| | SLENDID type 110 | 35 | 4.01 (original pH) | 2 | 4 |
| | | | 6.50 (adjusted pH) | 2 | 4 |
| POMOSIN GmbH | Type LM 12 CG | 35 | 2.75 (original pH)* | | |
| | | | 4.01 (adjusted pH)** | 4 | |
| Hercules (German) | | | 6.50 (adjusted pH) | 4 | 6 |
| | Type LM 18 CG | 40 | 2.74 (original pH)* | | |
| | | | 4.00 (adjusted pH)** | 6 | |
| | | | 6.50 (adjusted pH) | 4 | 8 |
| Sigma | Esterified Potassium salt | 31 | 5.13 (original pH) | 2 | 4 |
| | | | 6.50 (adjusted pH) | 2 | 4 |
| | Esterified Potassium salt | 67 | 4.62 (original pH)** | 9 | |
| | | | 6.50 (adjusted pH)** | 9 | |
| | Esterified | 93 | 2.88 (original pH)* | | |
| | | | 4.00 (adjusted pH)* | | |
| | | | 6.50 (adjusted pH)* | | |

*Gelling had not happened when the final concentration of pectin was varied from 2 to 10 g/l
**A solid gel had not formed when the final concentration of pectin was varied from 2 to 10 g/l

EXAMPLE 2

Nasal Drug Formulation Prepared from Pectins with Low DEs

Formulations were prepared containing drugs in the form of nicotine (a weak base) and cromolyn sodium (odium cronioglycate; a weak acid). Pectin formulations were prepared at a pectin concentration of 10 mg/mL using Slendid 100 and Slendid 110. The formulations were mixed with the simulated nasal electrolyte solution (the method of preparation of which was as in Example 1). The formulations were filled into a nasal delivery device (Pfeiffer metered dose pump) and the spray properties evaluated by visual examination.

The gelation of the formulation in the nasal electrolyte solution was evaluated as solution, gel or solid by visual observation and the flow properties before and after shaking. The results, which are set out in Table 2, show that when the formulation contained a weak acid (cromolyn sodium), gelation occurred in the nasal electrolyte solution. When the formulation contained a high level of a weak base (nicotine) then gelation did not occur.

The applicants believe that the reason for this difference is that the ionised nicotine may interact with the charged carboxyl groups on the pectin molecules and thereby influence the gelation characteristics of the low esterified pectin. Thus, with weakly basic drugs, a person skilled in the art is able to adjust the pectin concentration to take this interaction into account (see above).

TABLE 2

| | | | Mixing with simulated nasal electrolyte solution | | |
| --- | --- | --- | --- | --- | --- |
| Name | Sample | Spray property | Phase state | Flow Property | Phase state after shaking |
| G1 | 10 mg/ml pectin Slendid 100 | Good | Gel | – | Sol |
| G2 | 10 mg/ml pectin Slendid 110 | Good | Gel | – | Sol |
| G3 | Formulation I | Good | Sol | +++ | Sol |
| G4 | Formulation II | Good | Sol | +++ | Sol |
| G5 | Formulation III | Good | Gel | – | Sol |
| G6 | Formulation IV | Good | Gel | – | Sol |

Formulation I: 30.77 nicotine dihydrogen tartrate (10 mg/ml nicotine base) 10 mg/ml pectin 100
Formulation II: 30.77 nicotine dihydrogen tartrate (10 mg/ml nicotine base) 10 mg/ml pectin 110
Formulation III: 40 mg/ml cromolyn sodium salt/10 mg/ml pectin Slendid 100
Formulation IV: 40 mg/ml cromolyn sodium salt/10 mg/ml pectin Slendid 110
Flow properties:
–: non-flowing;
+++: flowing

EXAMPLE 3

To Demonstrate that Nasal Formulations Containing Low DE Pectin do not Enhance the Systemic Uptake of a Poorly Absorbed Drug For the local delivery of drugs it is important to retain the drug at its site of action, namely the nasal, rectal and vaginal cavities. In such cases, the formulation should not enhance the absorption of the drug. It is known that some bioadhesive gelling formulations may increase systemic uptake. Therefore, experiments have been conducted in an animal model to demonstrate that pectins with low DE do not enhance the nasal uptake (systemically) of a model polar drug, salmon calcitonin (S-CT).

Sheep

Eight female, cross-bred sheep of known weight were used in this study. The average weight of the sheep was in the region of 60 kg. The sheep were weighed and labelled 1 to 8. An in-dwelling Secalon cannula fitted with a flowswitch was placed approximately 15 cm into one of the external jugular veins of each animal on the first day of the study. Whenever necessary, the cannula was kept patent by flushing it with heparinised (25 IU/mL) 0.9% saline solution. This cannula remained in-dwelling in the jugular vein of each animal for the duration of the study and was removed upon completion of the study.

Preparation of Salmon Calcitonin (S-CT) Formulations

Two S-CT formulations were prepared. Each formulation contained 2000 IU/mL S-CT, which was sufficient material to administer a dose of 20 IU/kg in a volume of 0.01 mL/kg. The sheep were randomly divided into two groups of four animals and each group was dosed with a different S-CT formulation.

Summary of the Dose Groups

| Formulation | S-CT (IU/kg) | Chitosan G210 (mg/kg) | Pectin Slendid 100 (mg/kg) |
|---|---|---|---|
| I | 20 | — | — |
| II | 20 | — | 0.1 |

Prior to dose administration the sheep were sedated with an intravenous dose of Ketamine Vetalar® (100 mg/mL injection) at 2.25 mg/kg. Intranasal doses were administered at 0.01 mL/kg. The dose was divided equally between each nostril. For dose administration, a blueline umbilical cannula was inserted into the nostril of the sheep to a depth of 10 cm, before the delivery of the appropriate volume of solution from a 1 mL syringe.

Blood Sampling

Blood samples of 4 mL were collected from the cannulated jugular vein of the sheep at 15 and 5 minutes prior to S-CT administration and at 5, 15, 30, 45, 60, 90, 120, 150, 180, 240, 300, 360, 420 and 480 minutes post-administration. They were then mixed gently in 4 mL heparinised tubes and kept on crushed ice before plasma separation. Plasma was separated by centrifugation for 10 minutes at 4° C. approximately 3000 rpm. Each plasma sample was divided into two equal aliquots of approximately 1 mL and stored at −20° C. One set of plasma samples was used for calcium analysis.

Calcium Analysis

Plasma calcium analysis was performed by the Clinical Chemistry Department, Queens Medical Centre, University of Nottingham. The results showed that for the formulation I and II the plasma calcium levels were very similar and that the presence of pectin in the formulation did not lead to an increase in the systemic bioavailability of the model drug.

EXAMPLE 4

Simulated Nasal Electrolyte Solution-Pectin Gelling System for Controlled Release of Fexofenadine Hydrochloride Preparation of Formulations Formulation 1–10 mg/mL fexofenadine HCl/100 mg/mL HP-β-CD:

2 g of HP-β-CD was dissolved in 18–19 mL of water in a 20 mL volumetric flask. 200 mg of fexofenadine was added to the solution and stirred until the drug has dissolved. The pH of the solution was adjusted to 4.0, then the solution was made up to volume with water.

Formulation 2–10 mg/mL fexofenadine HCl/100 mg/mL HP-β-CD/10 mg/mL pectin 100:

50 mg of pectin 100 (SLENDID type 100, Hercules, Denmark) was dissolved in 5 mL of Formulation 1 in a 5 mL volumetric flask.

Release/Diffusion Testing

A Franz diffusion cell apparatus was set up in a closed loop arrangement and parameters were listed as follows:

Medium: Simulated nasal electrolyte solution

Temperature: 37° C.

Membrane: Cellulose nitrate, 0.45 µm pore size

Volume of the closed loop arrangement: 8.8 mL

Stirring speed of a magnetic stirrer: 4

Peristaltic pump flow rate: 1 (The Cole-Parmer Masterflex peristaltic pump, Model 7518-60, fitted with Masterflex L/Sth 14 silicone tubing)

Sample volume: 0.4 mL (contained 4 mg of fexofenadine HCl, the maximum concentration of the drug in medium will be around 450 µg/mL)

Wavelength: 260 nm

Results

Figure 2:
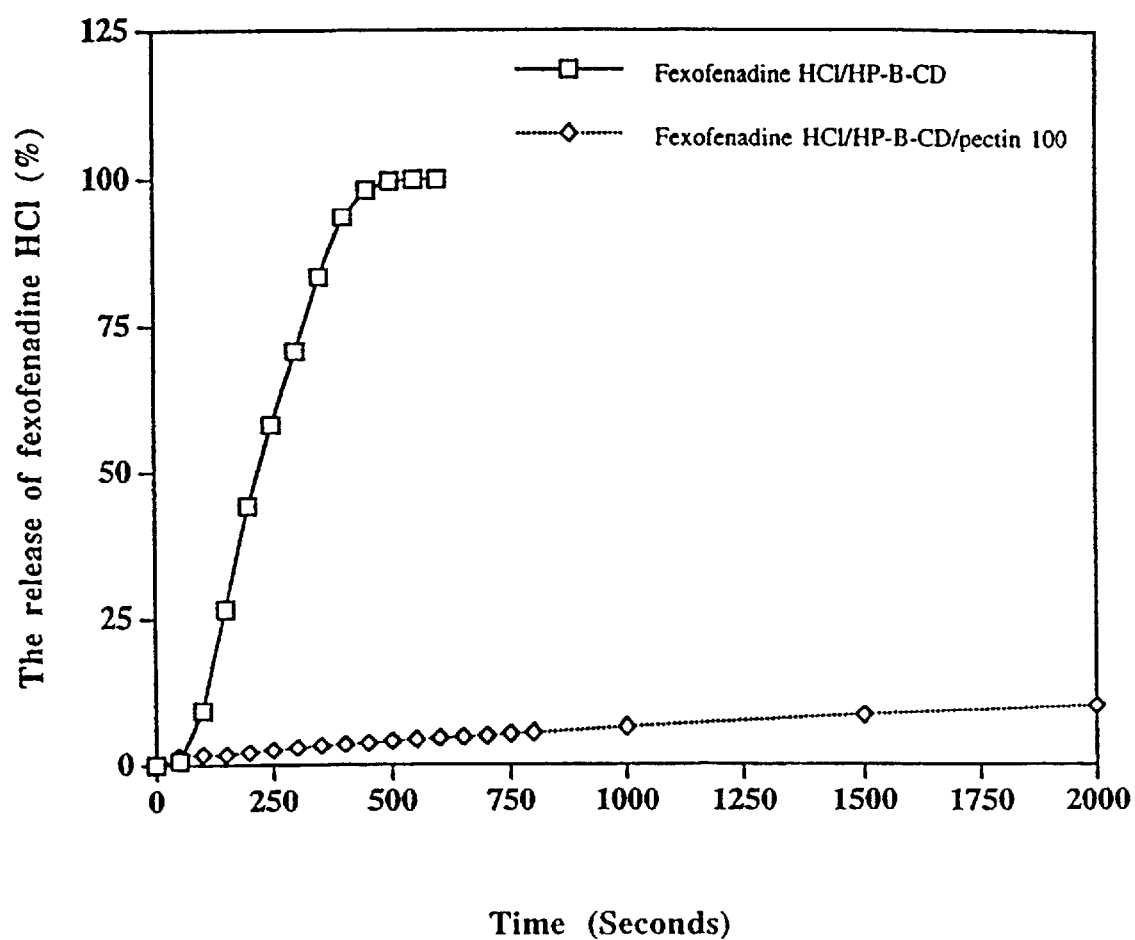
FIG. 2 shows the cumulative release/diffusion of fexofenadine HCl from HP-β-CD and HP-β-CD/pectin 100 solutions to simulated nasal electrolyte solution.

The results are shown in FIG. 2. (Every point on the graphs represents a mean value of two points.)

The maximum UV absorbance of Formulation 1 (control) reached during the diffusion experiment was used as 100% release to calculate the percentage of release at each selected time point.

The results show a clear difference in release characteristics of the two formulations.

We claim:

1. A liquid pharmaceutical composition for administration to a mucosal surface comprising a therapeutic agent, a pectin with a degree of esterification of less than 50%, and an aqueous carrier, wherein the composition gels or is adapted to gel at a site of application on the mucosal surface in the absence of an extraneous source of divalent metal ions.

2. The composition of claim 1 wherein the mucosal surface is the nasal cavity.

3. The composition of claim 1 wherein the mucosal surface is the vagina.

4. The composition of claim 1 wherein the mucosal surface is the rectum.

5. The composition of claim 1 wherein the mucosal surface is the back of the throat.

6. The composition of claim 1 wherein the mucosal surfaces is the eye.

7. The composition of claim 1 which is administered as a spray or a liquid free flowing system.

8. The composition of claim 1 wherein the pectin concentration in the composition is from 1 to 100 g/L.

9. The composition of claim 1 wherein the pH of the composition is between 2 and 9.

10. The composition of claim 1 wherein the therapeutic agent is an antiviral agent for delivery to the nose or the vagina.

11. The composition of claim 1 wherein the therapeutic agent is a vaccine for delivery to the nose, the rectum, or the vagina.

12. The composition of claim 1 wherein the therapeutic agent is a decongestant agent.

13. The composition of claim 1 wherein the therapeutic agent is a contraceptive agent.

14. The composition of claim 1 wherein the therapeutic agent is a vaginal lubricating agent.

15. The composition of claim 1 wherein the therapeutic agent is an anti-allergic agent.

16. The composition of claim 1 in a pharmaceutically acceptable dosage form suitable for administration to a mucosal surface.

17. The composition of claim 16 wherein the form is a spray or a liquid free flowing system.

18. A kit of parts comprising
   a liquid pharmaceutical composition for administration to a mucosal surface, the composition comprising a therapeutic agent, a pectin with a low degree of esterification, and an aqueous carrier, which composition gels or is adapted to gel at the site of application,
   wherein the kit does not include a solution of divalent metal ions to be added extraneously to the mucosal surface.

19. The kit of claim 18 further comprising instructions to administer the composition to the mucosal surface in the absence of an extraneous source of divalent metal ions.

20. A pharmaceutical gel composition obtained by applying a liquid composition, comprising a therapeutic agent, a pectin with a degree of esterification of less than 50% and an aqueous carrier, to a mucosal surface of a mammalian patient in the absence of extraneous application of a solution of divalent metal ions to the mucosal surface.

21. A method of treatment or prophylaxis of a disease comprising
   administering to a mucosal surface of a patient in need of the treatment or prophylaxis a liquid pharmaceutical composition, comprising a therapeutic agent which is effective against the disease, a pectin with a low degree of esterification, and an aqueous carrier, which composition gels or is adapted to gel at the site of administration in the absence of extraneous application of a solution of divalent metal ions to the mucosal surface.

22. The method of claim 21 wherein the patient is a mammal.

23. A method for the delivery of therapeutic agents to a mucosal surface in a mammal, which method comprises
   administering a liquid pharmaceutical composition, comprising a therapeutic agent, a pectin with a degree of esterification of less than 50%, and an aqueous carrier, which composition gels or is adapted to gel at the site of administration in the absence of extraneous application of a solution of divalent metal ions to the mucosal surface.

24. A process for the preparation of a liquid pharmaceutical composition comprising
   providing a therapeutic agent, a pectin with a degree of esterification of less than 50%, and an aqueous carrier; and
   mixing together the therapeutic agent and the pectin in the aqueous carrier to form a liquid composition that gels or is to gel at a site of administration on a mucosal surface in the absence of extraneous application of a solution of divalent metal ions to the mucosal.

* * * * *

UNITED STATES PATENT AND TRADEMARK OFFICE
CERTIFICATE OF CORRECTION

| | | |
|---|---|---|
| PATENT NO. | : 6,432,440 B1 | Page 1 of 1 |
| APPLICATION NO. | : 09/402976 | |
| DATED | : August 13, 2002 | |
| INVENTOR(S) | : Peter James Watts | |

It is certified that error appears in the above-identified patent and that said Letters Patent is hereby corrected as shown below:

Column 16, line 29, after "mucosal" and before the period, please add --surface--.

Signed and Sealed this

Fifth Day of June, 2007

JON W. DUDAS
*Director of the United States Patent and Trademark Office*